(12) United States Patent
Nakamura

(10) Patent No.: US 6,210,035 B1
(45) Date of Patent: Apr. 3, 2001

(54) HIGH-SPEED THERMAL ANALYZER

(75) Inventor: Nobutaka Nakamura, Chiba (JP)

(73) Assignee: Seiko Instruments Inc. (JP)

(*) Notice: Subject to any disclaimer, the term of this patent is extended or adjusted under 35 U.S.C. 154(b) by 0 days.

(21) Appl. No.: 09/200,311

(22) Filed: Nov. 25, 1998

(30) Foreign Application Priority Data

Nov. 28, 1997 (JP) .................................................. 9-328727

(51) Int. Cl.[7] .......................... G01N 25/00; G01K 17/08
(52) U.S. Cl. .................... 374/11; 374/10; 374/29; 374/30; 374/39
(58) Field of Search ........................ 374/11, 14, 55, 374/56, 13, 12, 57, 31, 10, 29, 30, 39

(56) References Cited

U.S. PATENT DOCUMENTS

| | | | |
|---|---|---|---|
| 3,283,560 | * 11/1966 | Harden et al. ......................... | 374/12 |
| 3,524,340 | * 8/1970 | Krakovetsky-Kocherzhinsky et al. ............................................................. | 374/13 |
| 3,675,465 | * 7/1972 | Sommer et al. ......................... | 73/15 |
| 4,838,706 | * 6/1989 | Coey et al. ............................. | 374/54 |
| 5,174,655 | * 12/1992 | Litz et al. ............................. | 374/31 |
| 5,193,910 | * 3/1993 | Kinoshita ............................... | 374/57 |
| 5,300,888 | * 4/1994 | Webster et al. ....................... | 324/315 |
| 5,493,078 | * 2/1996 | Uchike ................................. | 177/212 |
| 5,826,983 | * 10/1998 | Nakamura et al. ..................... | 374/14 |
| 6,079,873 | * 6/2000 | Cavicchi et al. ....................... | 374/10 |
| 6,099,162 | * 8/2000 | Walsh ................................... | 374/30 |
| 6,146,013 | * 6/2000 | Huetter et al. ......................... | 374/46 |

* cited by examiner

*Primary Examiner*—G. Bradley Bennett
*Assistant Examiner*—G. Verbitsky
(74) *Attorney, Agent, or Firm*—Adams & Wilks

(57) ABSTRACT

A thermal analyzer includes a processor for processing a thermal analysis signal of a sample obtained by performing high-speed thermal analysis of the sample at an experimental heating rate. The processor includes a peak component calculator for calculating peak components of the thermal analysis signal, an activation energy calculator for calculating activation energy values based on the peak components of the thermal analysis signal, and a heating rate conversion and output device for estimating a second thermal analysis signal that would be obtained under a thermal analysis of the sample conducted at a desired heating rate different from the experimental heating rate based on the experimental heating rate and the activation energy values obtained by the activation energy calculator, the second thermal analysis signal being calculated based on the thermal analysis signal obtained at the experimental heating rate. The experimental heating rate may be faster than the desired heating rate, so that the second thermal analysis signal may be estimated by performing an accelerated thermal analysis of the sample at the experimental heating rate.

52 Claims, 1 Drawing Sheet

11: PID CONTROL CIRCUIT
12: CURRENT DETECTOR
13: DIFFERENTIAL AMPLIFIER
14: DIFFERENTIATOR CIRCUIT
15: TEMPERATURE-MEASURING CIRCUIT
17: TEMPERATURE CONROL CIRCUIT
16: FUNCTION GENERATOR
18: PROCESSOR
19: WAVEFORM ANALYZER
20: ACTIVATION ENERGY-CALCULATING UNIT
21: HEATING RATE CONVERSION AND OUTPUT DEVICE

11: PID CONTROL CIRCUIT
12: CURRENT DETECTOR
13: DIFFERENTIAL AMPLIFIER
14: DIFFERENTIATOR CIRCUIT
15: TEMPERATURE-MEASURING CIRCUIT
17: TEMPERATURE CONROL CIRCUIT
16: FUNCTION GENERATOR
18: PROCESSOR
19: WAVEFORM ANALYZER
20: ACTIVATION ENERGY-CALCULATING UNIT
21: HEATING RATE CONVERSION AND OUTPUT DEVICE

HIGH-SPEED THERMAL ANALYZER

BACKGROUND or THE INVENTION

The present invention relates to a thermal analyzer for measuring a signal indicating variations in the physical or chemical nature of a sample as a function of temperature or time. More particularly, the invention relates to a novel thermal analyzer which permits the interchange of thermal analysis data arising from different heating rates of a sample and which, at the same time, allows a thermal analysis of the sample to be performed in a greatly shortened time.

Thermal analysis is a powerful means for investigating how a physical property of a material or sample varies with temperature.

Typical thermal analyzers include the differential scanning calorimeter (DSC), differential calorimeter (DTA), thermogravimetry instrument (TG), and thermomechanical analyzer (TMA). These instruments measure enthalpic balance of samples, differential temperatures (qualitative enthalpic balance), weights, and the dependence of various lengths on temperature (variations in physical or chemical properties of samples), respectively.

In thermal analysis, a physical property of a sample and temperature variations are continuously measured while heating the sample at a given rate. At this time, the dependence of the physical property of the sample on temperature can be derived from the relation between the temperature signal and the physical property signal. Various thermal analyzers for performing analysis of this kind are commercially available and used industrially for research and quality control purposes.

In the prior art thermal analysis described above, it is customary to heat a sample at a rate of 5 to 20 degrees/min. For example, if a temperature range of about 1000 degrees is scanned, it takes 1 to 3 hours to complete the scan. In view of this, the prior art analysis has disadvantage in that the time efficiency is low.

An ordinary thermal analyzer can perform a measurement operation at a heating rate of 50 to 100 degrees/sin. This shortens the measuring time. In spite of this, relatively low heating rates of 5 to 20 degrees/min are often used for the following primary reason. If a sample inducing plural reactions during scanning of the temperature is heated at a high rate, these reactions tend to overlap. The resulting data is inevitably cumbersome to analyze.

Thermal analysis is intended to investigate the dependence of a physical property of a sample on temperature. Detailed investigation of the measured signal indicating the physical property has shown that the physical property signal is observed to depend on time as well as on temperature in practice. The two main reasons for this are:

1) A detector for detecting variations in the physical property of the sample has intrinsic time constant.

2) The function of temperature is not the total amount of reactions induced in the sample but the reaction rate (i.e., the reaction ratio per unit time).

After thermal analysis of a sample is conducted at a varying heating rate, it measured data are simply taken as physical property values that are functions of temperature, and if they are compared, then results of the measurement are that the same sample shows different decomposition and reaction temperatures reflecting the time dependence effects of the physical property.

SUMMARY OF THE INVENTION

To quickly solve the problems with the prior art technique described above, the present invention provides: means for heating a sample at an experimental heating rate and producing a thermal analysis signal indicating how the physical property of the sample varies with temperature; an analyzer for analyzing variations in the thermal analysis signal by dividing the signal into plural overlapping fundamental elements; an activation energy-calculating unit for calculating activation energies corresponding to the fundamental elements analyzed by the analyzer; and a heating rate conversion and output device for estimating a thermal analysis signal that should be obtained when a measurement is made at a desired heating rate, based on the experimental heating rate and from the activation energy values obtained by the activation energy-calculating unit, and for producing the thermal analysis signal.

With the aforementioned structure, the sample is heated at an experimental heating rate. A thermal analysis signal is obtained by actual measurement. Then, a thermal analysis signal that should be obtained at a desired heating rate is estimated from the obtained thermal analysis signal and produced. In this manner, thermal analysis results are obtained under desired heating rate conditions. As a result, the measurement time is shortened. The reaction temperature can be compared among different data arising from different heating, rates.

DETAILED DESCRIPTION OF THE INVENTION

Figure 1:
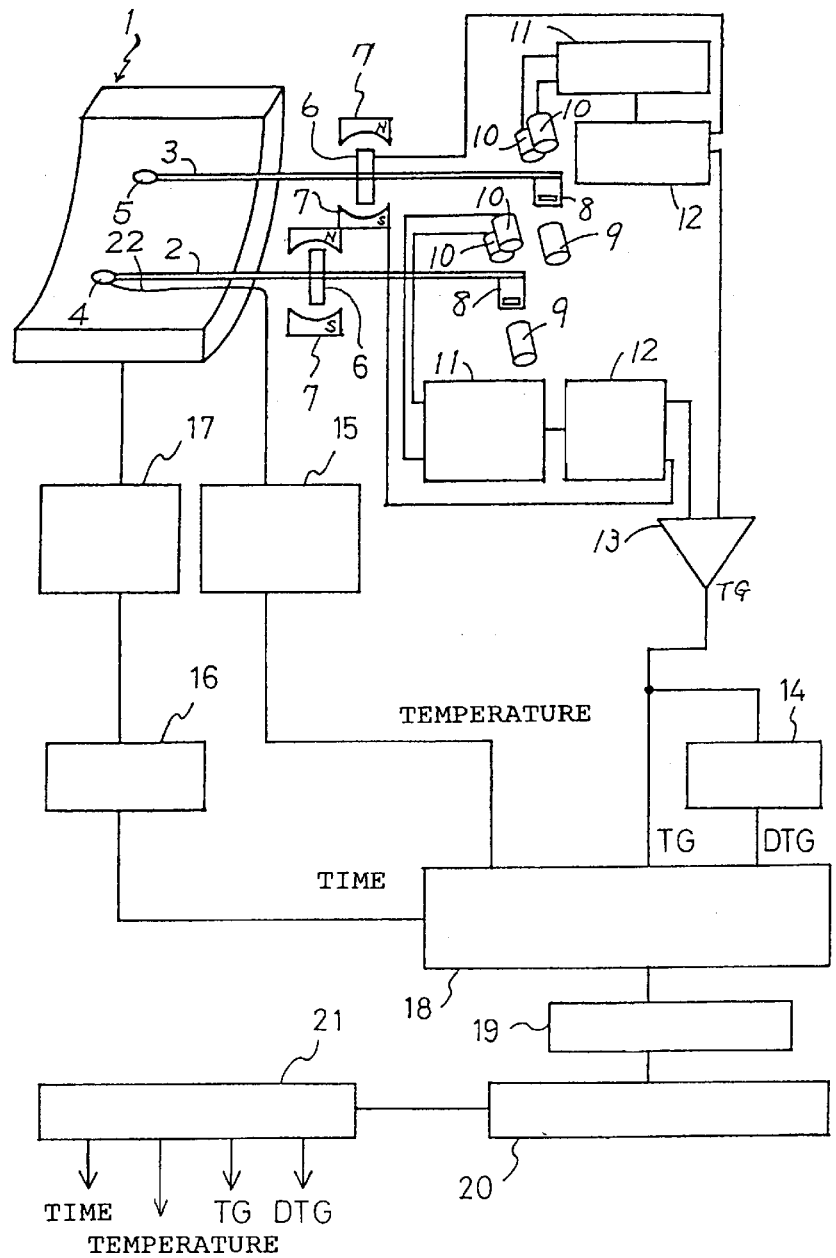
FIG. 1 is a block diagram of a TG measuring instrument that. is one example of the present invention.

An example of the present invention is hereinafter described with reference to the attached drawing.

FIG. 1 is a schematic block diagram of a TG. A heating furnace 1 for heating a sample and a reference sample is cylindrical, can heat up to 1500 degrees at a rate of less than 100 degrees/min. A pair of beams, or a sample beam 2 and a reference beam 3, are inserted horizontally in the heating furnace 1. A sample holder 4 is fixedly mounted at the front end of the sample beam 2. A reference holder 5 is fixed at the front end of the reference beam 3. A sample (not shown) to be thermally analyzed by TG is placed on the sample holder 4. A reference substance (not shown) that is chemically and thermally stable is placed on the reference holder 5. Coils 6 are fixed at the centers of the beams 2 and 3, respectively. The coils 6 are placed within magnetic fields developed by magnets 7, respectively. Lead wires (not shown) from the coils 6 hold the beams 2 and 3 in the vertical direction. The beams 2 and 3 can rotate as a whole.

Slits 8 are attached to the other ends of the beams 2 and 3, respectively. Lamps 9 are mounted adjacent the slits 8, respectively, so that light passes therethrough. Photodiodes 10 are fixed at positions to receive light passed through the slits 8, respectively. Signals from the photodiodes 10 are input to PID controllers 11, respectively. Their outputs are supplied to current detectors 12, respectively. Amounts of currents to be fed back to the coils 6 to maintain the beams 2 and 3 horizontal are detected and supplied. Electric currents supplied to the coils 6 cooperate with the magnets 7 and the coils 6 to apply a torque to the beams 2 and 3 in directions effective to suppress or prevent displacements of the beams 2 and 3.

A feedback control system consisting of the aforementioned coils 6, magnets 7, slits 8, lamps 9, photodiodes 10, PID controllers 11, and current detectors 12 is kept in operation during the operation of TG. Therefore, even if the sample placed on the sample holder 4 usually decomposes and its weight varies, the beams 2 and 3 remain in place as if they were at rest.

Signals from the current detectors 12 are also supplied to a differential amplifier 13, respectively, which produces the difference between a current value necessary to bring the sample beam 2 to a stop and a current value necessary to bring the reference beam 3 to a stop and amplifies the difference. That is, the output from the differential amplifier 13 represents the difference in the torques necessary to return the sample beam 2 and the reference beam 3 to their original states.

A thermally stable reference substance is placed on the reference holder 5. A sample to be measured is placed on the sample holder 4. If thermal analysis is performed under this condition, the output from the differential amplifier 13 represents variations in the weight of the sample provided that the output is appropriately normalized (i.e., if multiplied by an appropriate coefficient). The output represents thermogravimetric (TG) signal, i.e., variations in a physical property of the sample. The TG signal produced by the differential amplifier 13 is sent to a differentiator circuit 14, which differentiates its input with respect to time. The signal is then inverted in sign and delivered as a derivative TG (DTG) signal. The TG signal often treats decreases in weight due to decompositions. To normalize the DTG signal so that one can easily see the signal, the sign is inverted for convenience.

A thermocouple (not shown) for measuring the temperature of the sample is fixed to the bottom surface of the sample holder 4. Signal lines from the thermocouple are connected to a temperature-measuring circuit 15 from the vicinities of the centers of the beams 2 and 3 by thin lines 22 having a diameter of 50 microns formed on springs to prevent the torque applied to the sample beam 2 from being affected. In the FIGURE, the thin lines 22 are shown to be linear. As a result, a sample temperature signal is produced by the temperature-measuring circuit 15.

The temperature of the heating furnace 1 can be programmed and controlled according to a temperature signal that is a ramp function of time. The temperature of the heating furnace 1 is accurately controlled according to the output from a function generator 16 by the operation of a temperature control circuit 17, the function generator 16 producing the programmed temperature signal. In consequence, the temperature of the sample is controlled at the heating rate programmed into the function generator 16.

The function generator 16 generates the aforementioned temperature program function, and is connected with a processor 18. The function generator 16 sends a time signal indicating the time elapsed since the start of measurement to the processor 18. The time signal from the function generator 16, the TG signal from the differential amplifier 13, the DTG signal from the differentiator circuit 14, and the temperature signal from the temperature-measuring circit 15 are sent to the processor 18. These signals are managed as thermal analysis data.

The thermal analysis data from the processor 18 is sent to a waveform analyzer 19 connected with the processor 18. The waveform analyzer 19 detects successive peaks of the DTG signal from the thermal analysis data and appropriately analyzes the peaks such that overlapping peaks are represented as superimposition of individual peaks.

The thermal analysis data and information about the temperature range of the DTG peak signals are sent to an activation energy-calculating unit 20 connected with the waveform analyzer 19, the DTG peak signals being analyzed by the waveform analyzer 19. The activation energy-calculating. unit 20 calculates activation energies corresponding to DTG peaks from the thermal analysis data within the temperature range in which the analyzed DTG peak signals do not overlap. A well-known method known as the Freeman-Carroll method is used as the method of calculating the activation energies.

The thermal analysis data, the analyzed DTG peak signals, their temperature range, and information about the activation energy values corresponding to the DTG peaks are sent to a heating rate conversion and output device 21 connected with the activation energy-calculating unit 20. The heating rate conversion and output device 21 calculates temperature deviations at individual points of the DTG peaks that should be produced when measurements are made, from the values of the activation energy for the DTG peaks according to the Arrhenius law representing the relation between the temperature of the reaction in the sample and time. The calculating unit again superimposes the individual DTG peak signals that are shifted in temperature by amounts corresponding to the temperature deviations, inverts the resulting signal, and integrates it with respect to time, thus calculating the TG signal. In this way, the heating rate conversion and output device 21 estimates the thermal analysis signal that should be obtained, and produces it.

An actual example of measurement performed using the present instrument is next described. A thermally stable reference substance (e.g., an appropriate amount of powdered alumina put in a platinum container) is placed on the reference holder 5 together with its container. A sample to be subjected to TG measurement is placed on the sample holder 4 together with its container.

A temperature program used for measurements is entered into the function generator 16. The temperature program sets a start temperature, an end temperature, and a heating rate in the interval between both temperature. An appropriate temperature program is used according to the nature of the sample and the purpose of measurement. A typical example of the temperature program is used to heat from room temperature to 1200 degrees at a rate of 10 degrees/min. If a measurement is executed under this program, it takes about 2 hours for the measurement. If the heating rate is increased, the measuring time will be shortened. However, varying the heating rate will change the reaction temperature and separate reactions to a lesser extent. Consequently, it is more difficult to see the reactions. For these reasons, the heating rate used for actual thermal analysis is roughly from 5 degrees to 20 degrees/min.

However, in the present embodiment, the action of the waveform analyzer 19, the activation energy-calculating unit 20, and the heating rate conversion and output device 21 can eliminate the drawback created by performing measurements at increased heating rates. Therefore, measurements are performed with a temperature program with 50 degrees/min. During measurement, signals indicating the elapsed time, the sample temperature, the sample weight (TG), and time-derivative TG (hereinafter referred to as DTG) are accepted as sets of thermal analysis data into the processor 18 via an analog-to-digital converter (not shown) at given sampling intervals and stored there.

After the end of the measurement, the thermal analysis data accepted into the processor 18 is sent to the waveform analyzer 19, which examines the number of peaks contained in the DTG signal and how they overlap. The number of peaks and how they overlap are examined by the following procedure:

1) The second-order derivative of the DTG signal with respect to time is calculated while performing appropriate smoothing processing.

2) The second-order derivative signal found in 1) is differentiated with respect to time, thus obtaining a third-order derivative signal.

3) Each point where the third-order derivative signal is zero and, at the same time, the second-order derivative signal assumes a negative minimum value is taken as a peak position. The number of the peak positions is found.

4) If plural peak positions are present, and if the DTG signal is zero at every point between the adjacent peaks, the situation is regarded as "no peak overlap". In other cases, the situation is regarded as "overlap of peaks".

5) If overlap of peaks exists, the waveform analyzer 19 separates the individual peaks according to a well-known overlapping waveform-analyzing procedure such as Symplex method or Gauss-Newton Method.

6) If adjacent peaks overlap, the maximum value of the second-order derivative signal of the DTG existing between the peak positions is taken as a "peak boundary". If the adjacent peaks do not overlap, one of points at which the DTG signal is zero between the adjacent peak is taken as a "peak boundary".

The activation energy-calculating unit 20 calculates the activation energies of the DTG signal peaks at the peak positions separated by the procedure described above from the Freeman-Carroll method. During this process, only the number of peaks is obtained. It is assumed that the activation energies have values within every time range of the thermal analysis data and take the form of a step function whose value varies across every peak boundary.

A heating rate conversion and output device 21 calculates thermal analysis data that should be obtained when the heating rate is converted from 50 degrees/min used in actual measurements to 10 degrees/min. The conversion is made for each peak of the DTG signals, based on the values of the activation energies. The calculations are performed as follows:

The reaction rate in the case of a single reaction is expressed in terms of the Arrhenius law.

$$dx/dt = -A \cdot \exp(-\Delta E/RT) g(x) \quad (1)$$

where x is the amount of chemical structure created or decreased by the reaction, t is time, A is a frequency factor (constant), $\Delta E$ is activation energy, R is a gas constant, T is absolute temperature, and g is a function of x.

On the other hand, in thermal analysis where measurements are made at a given heating rate of B degrees/min, the following relation holds between time t and temperature T:

$$T(t) = a + B \cdot t \quad (2)$$

where a is a constant. Accordingly, $$dt = dT/B \quad (3)$$

Eq. (3) is substituted into Eq. (1) to separate the variables x and T. Thus, $$dx/g(x) = (A/B) \cdot \exp(-\Delta E/RT) \cdot dT \quad (4)$$

Taking the natural logarithms of both sides and rearranging the equation with an appropriate approximation gives rise to $$lnB_1 = -(\Delta E/R)(l/T) + lnA - ln\{dx/g(x)\} \quad (5)$$

Eq. (5) can be interpreted as follows: If the heating rate is $B_1$ degrees/min, per minute, the reaction ratio reaches x at temperature T. Consider a point where the reaction ratio assumes a certain value $x_0$. When the heating rate is $B_1$ degrees/min, the reaction ratio is $x_0$ at a temperature of $T_1$. When the reaction ratio is $B_2$ degrees/min, the reaction ratio is $x_0$ at a temperature of $T_2$. The second term of the right side is a constant. If a point where the reaction ratio assumes a given value $x_0$ is taken into account, the third term of the right side is also constant. Let C (constant) be the sum of the second and third terms of the right side. The relation described above is expressed by the following simultaneous equations:

$$lnB_1 = -(\Delta E/RT_1) + C \quad (6)$$

$$lnB_2 = -(\Delta E/RT_2) + C \quad (7)$$

C is removed from Eqs. (6) and (7). Solving them with respect to $T_2$ gives rise to $$T_2 = l/\{(l/T_1) + (R/\Delta E) \cdot ln(B_1/B_2)\} \quad (8)$$

Eq. (8) indicates that the point of temperature $T_1$ in each of the peak waveforms of the separated DTG signals should be shifted to temperature $T_2$ in order to convert thermal analysis data measured at heating rate $B_1$ degrees/min into data about heating rate $B_2$ degrees/min. All the DTG peak waveforms obtained in this way are summed up. Consequently, the whole DTG signal that should be obtained when a measurement is made at the heating rate of $B_2$ degrees/min is estimated. Finally, the TG signal is obtained by inverting the sign of the DTG signal and integrating the signal with respect to time.

In the illustrative embodiment, the TG instrument has been described. Obviously, the invention can be applied to the other thermal analyzers described in the term "Prior Art Technique".

In summary, the present invention is a high-speed thermal analyzer comprising: a means for heating a sample at an experimental heating rate and producing a thermal analysis signal indicating how a physical property of the sample varies with temperature; an activation energy-calculating unit for calculating an activation energy from said thermal analysis signal; and a heating rate conversion and output device for estimating a thermal analysis signal that should be obtained when a measurement is made at a desired heating rate, from said experimental heating rate and from the value of the activation energy obtained by the activation energy-calculating unit, and for producing the thermal analysis signal, whereby a thermal analysis signal that should be obtained at another heating rate is obtained from the thermal analysis signal derived from the experimental heating rate. In addition, the invention is a high-speed thermal analyzer comprising: a means for heating a sample at an experimental heating rate and producing a thermal analysis signal indicating how a physical property of the sample varies with temperature; an analyzer for analyzing variations in said thermal analysis signal into plural overlapping fundamental elements; an activation energy-calculating unit for calculating activation energies corresponding to the fundamental elements analyzed by said analyzer; and a heating rate conversion and output device for estimating a thermal analysis signal that should be obtained when a measurement is made at a desired heating rate, from said experimental heating rate and from the values of the activation energy obtained by the activation energy-calculating unit, and for producing the thermal analysis signal, whereby a thermal analysis signal that should be obtained at another heating rate is obtained from a thermal analysis signal derived from the experimental heating rate.

Since the invention is constructed as described thus far, a measurement can be completed in a time that is reduced by a factor of 5 using an instrument in accordance with the present invention by performing the measurement at an experimental heating rate of 50 degrees/min, for example, and then converting data into data that would be obtained at a heating rate of 10 degrees/min. The measuring efficiency can be enhanced by the great reduction in the measuring time. Furthermore, the present invention produces the advantage that deterioration of the ability to separate reactions intrinsic in high-speed temperature elevation does not take place, because the dependence on time contained in the measured data is converted into deviations of the measuring temperature and corrections are made. Additionally, in accordance with the invention, data arising from different heating rates during measurement are converted into the same heating rate conditions and data about samples can be compared. Consequently, the reaction temperatures of the samples can be compared precisely in spite of different heating rate conditions.

What is claimed is:

1. A high-speed thermal analyzer comprising:
   heating means for heating a sample at an experimental heating rate and producing a first thermal analysis signal indicating how a physical property of the sample varies with temperature;
   an activation energy calculating unit for calculating an activation energy based on the first thermal analysis signal; and
   a heating rate conversion and output device for estimating a second thermal analysis signal that would be obtained under a thermal analysis of the sample performed at a desired heating rate different from the experimental heating rate, based on the experimental heating rate and the activation energy obtained by the activation energy-calculating unit, whereby the second thermal analysis signal that would be obtained at the desired heating rate is obtained based on the first thermal analysis signal derived by performing thermal analysis at the experimental heating rate.

2. A high-speed thermal analyzer comprising:
   means for heating a sample at an experimental heating rate and producing a first thermal analysis signal indicating how a physical property of the sample varies with temperature;
   an analyzer for analyzing variations in the thermal analysis signal by dividing the thermal analysis signal into plural overlapping fundamental elements;
   an activation energy calculating unit for calculating an activation energy value corresponding to each of the fundamental elements obtained by the analyzer; and
   a heating rate conversion and output device for estimating a second thermal analysis signal that would be obtained under a thermal analysis of the sample performed at a desired heating rate different from the experimental heating rate, based on the experimental heating rate and the activation energy values obtained by the activation energy calculating unit, and for producing the second thermal analysis signal, whereby the second thermal analysis signal that would be obtained at the desired heating rate is obtained based on the thermal analysis signal derived by performing thermal analysis at the experimental heating rate.

3. A high-speed thermal analyzer according to claim 1; wherein the experimental heating rate is faster than the desired heating rate, so that the second thermal analysis signal may be estimated by performing an accelerated thermal analysis of the sample at the experimental heating rate.

4. A high-speed thermal analyzer according to claim 1; wherein the means for heating comprises a furnace having a sample container in which the sample and a reference substance are heated, temperature detecting means for detecting the temperature of the sample and the reference substance, and a temperature control circuit for controlling the furnace temperature according to the experimental heating rate.

5. A high-speed thermal analyzer according to claim 4; wherein the heating furnace is cylindrical.

6. A high-speed thermal analyzer according to claim 4; wherein the heating furnace can heat the sample to 1500° C. at a rate of 100 degrees/minute.

7. A high-speed thermal analyzer according to claim 4; further comprising means for producing the first thermal analysis signal by comparing a physical characteristic of the sample with a physical characteristic of the reference substance during thermal analysis performed at the experimental heating rate and outputting the first thermal analysis signal based on the comparison result.

8. A high-speed thermal analyzer according to claim 7; wherein the means for producing the first thermal analysis signal comprises a sample support beam having a first end extending into the furnace for supporting the sample and a reference support beam having a first end extending into the furnace for supporting the reference substance, the sample support beam and the reference support beam being vertically balanced and supported so as to be free to undergo rotational movement about a longitudinal axis thereof as a result of physical decomposition of the sample and the reference substance, respectively.

9. A high-speed thermal analyzer according to claim 8; further comprising a sample holder fixedly mounted at the first end of the sample beam for supporting the sample and the sample container, and a reference substance holder fixedly mounted at the first end of the reference beam for supporting the reference substance and a reference substance container.

10. A high-speed thermal analyzer according to claim 9; wherein the sample is disposed in the sample container on the sample holder and a chemically and thermally stable reference substance is disposed in the reference container on the reference holder so that the sample undergoes decomposition during thermal analysis but the reference substance does not undergo decomposition during thermal analysis.

11. A high-speed thermal analyzer according to claim 10; wherein the means for producing the first thermal analysis signal further comprises a feedback control system for maintaining the sample beam and the reference beam at fixed orientations about longitudinal axes thereof so that decomposition of the sample during thermal analysis does not cause the sample beam to undergo rotational movement.

12. A high-speed thermal analyzer according to claim 11; wherein the feedback control system comprises a coil formed around a portion of each beam, magnets disposed adjacent the coils, and detecting means for detecting rotational movement of the respective beams and outputting a corresponding signal used to drive the coils so as to cooperate with the adjacent magnets to maintain the beams in a stationary position.

13. A high-speed thermal analyzer according to claim 12; wherein the detecting means comprises a slit formed at a second end of each of the beams opposite the first end, a light emitting element mounted adjacent each slit to project light therethrough, photodiodes disposed adjacent each slit for receiving light that has passed through the respective slits and outputting a corresponding signal, position detection elements connected to the photodiodes for detecting an angular position of the beams based upon output signals of the photodiodes and outputting a corresponding output signal, and current detectors for receiving the output signals of the position detection elements and for supplying a current to the respective coils to maintain the beams in a constant orientation.

14. A high-speed thermal analyzer according to claim 13; wherein the position detection elements comprise PID controllers.

15. A high-speed thermal analyzer according to claim 14; wherein the means for producing the first thermal analysis signal further comprises a differential amplifier for receiving outputs of the current detectors and producing an amplified difference signal representing a difference in current values necessary to maintain the sample beam and the reference beam at rest.

16. A high-speed thermal analyzer according to claim 15; wherein the amplified difference signal comprises the first thermal analysis signal.

17. A high-speed thermal analyzer according to claim 16; further comprising a differentiator circuit for differentiating the first thermal analysis signal with respect to time and outputting a differentiated thermal analysis signal.

18. A high-speed thermal analyzer according to claim 17; further comprising a programmable temperature control circuit for controlling the temperature of the furnace.

19. A high-speed thermal analyzer according to claim 18; further comprising a function generator for storing a temperature program for driving the temperature control circuit to heat the sample and the reference substance and outputting a time signal indicating the elapsed time since the start of a measurement.

20. A high-speed thermal analyzer according to claim 19; wherein the temperature program comprises a program for increasing the furnace temperature according to a ramp function of time.

21. A high-speed thermal analyzer according to claim 19; wherein the temperature program comprises a start temperature at which thermal analysis of the sample is to begin, an end temperature at which the thermal analysis is to end, and a temperature rate at which the temperature of the sample is to be increased during the thermal analysis.

22. A high-speed thermal analyzer according to claim 16; further comprising a processor; and wherein the time signal from the function generator, the output signal of the differential amplifier, the output signal from the differentiator circuit, and a temperature signal output by the temperature detecting means are supplied to the processor as thermal analysis data.

23. A high-speed thermal analyzer according to claim 22; further comprising a waveform analyzer connected to the processor for detecting successive peaks of the output signal of the differentiator circuit and analyzing the peaks such that overlapping peaks are represented as the superposition of individual peaks.

24. A high-speed thermal analyzer according to claim 23; wherein the activation energy calculating unit is connected to the waveform analyzer for receiving the thermal analysis data and peak data from the waveform analyzer and for calculating activation energies corresponding to the peaks within temperature ranges at which the analyzed peak signals do not overlap.

25. A high-speed thermal analyzer according to claim 24; wherein the activation energy calculating unit calculates the activation energies of the peaks according to the Freeman-Carroll method.

26. A high-speed thermal analyzer according to claim 25; wherein the heating rate conversion and output device is connected to the activation energy calculation unit and receives the thermal analysis data, the analyzed peak data, the temperature range of the peaks, and the activation energy values corresponding to the peaks, and calculates the second thermal analysis signal on the basis thereof.

27. A high-speed thermal analyzer according to claim 26; wherein the heating rate conversion and output device calculates the second thermal analysis signal based upon the Arrhenius law, reflecting the relation between temperature of the reaction in the sample and time.

28. A high-speed thermal analyzer according to claim 27; wherein the reference substance is alumina.

29. A thermal analyzer comprising: means for heating a sample at an experimental heating rate and producing a first thermal analysis signal indicating a relationship between a variation in a physical property of the sample with respect to temperature; and processing means for processing the thermal analysis signal obtained during thermal analysis of the sample at the experimental heating rate, the processing means including means for obtaining peak components of the thermal analysis signal, an activation energy calculator for calculating activation energy values based on the peak components of the thermal analysis signal, and a heating rate conversion and output device for estimating a second thermal analysis signal that would be obtained under a thermal analysis of the sample conducted at a desired heating rate different from the experimental heating rate based on the experimental heating rate and the activation energy values obtained by the activation energy calculator, the second thermal analysis signal being calculated based on the thermal analysis signal obtained at the experimental heating rate.

30. A thermal analyzer according to claim 29; wherein the experimental heating rate is faster than the desired heating rate, so that the second thermal analysis signal may be estimated by performing an accelerated thermal analysis of the sample at the experimental heating rate.

31. A thermal analyzer according to claim 29; wherein the means for heating comprises a furnace having an internal chamber having a sample support that is movable in response to decomposition of the sample, a symmetrically arranged reference substance support that is movable in response to decomposition of the reference substance, and means for maintaining the sample support and the reference substance support in a constant orientation and outputting a signal corresponding to a relative amount of control required to maintain the sample support and reference substance support in the constant orientation.

32. A thermal analyzer according to claim 31; further comprising a function generator for outputting a temperature control signal to control the furnace temperature according to a predetermined temperature control program, and for outputting an elapsed time signal.

33. A thermal analyzer according to claim 32; wherein the temperature program comprises a start temperature at which thermal analysis of the sample is to begin, an end temperature at which the thermal analysis is to end, and a temperature rate at which the temperature of the sample is to be increased during the thermal analysis.

34. A thermal analyzer according to claim 29; wherein the processing means further comprises separating means for separating the first thermal analysis signal into a plurality of components by calculating a second order derivative of the thermal analysis signal, assigning as peak regions those regions of the first thermal analysis signal where the value of the second order derivative deviates outside a threshold range, and subtracting a baseline component of the thermal analysis signal from the first thermal analysis signal to obtain the peak component.

35. A thermal analyzer according to claim 29; wherein the processing means further comprises a separator for separating the peak component into a plurality of peak elements and outputting peak data.

36. A thermal analyzer according to claim 35; wherein the separator comprises differentiating means for taking the second-order derivative and the third-order derivative of the peak component with respect to time, assigning as a peak position of the first thermal analysis signal each point at which the third-order derivative of the peak component is equal to zero and, at the same time, the second-order derivative signal has a negative minimum value, counting the number of peak positions and separating overlapping peaks using an overlapping waveform-analyzing procedure.

37. A thermal analyzer according to claim 36; further comprising means for integrating the peak data with respect to time.

38. A thermal analyzer according to claim 37; wherein the activation energy calculator includes means for calculating the activation energy of the peaks separated by the separator based on the temperature, peak data and peak integration data.

39. A thermal analyzer according to claim 29; wherein the heating rate conversion and output device includes means for amplifying a baseline and adding data.

40. A thermal analyzer according to claim 29; wherein the reference substance is alumina.

41. A thermal analyzer comprising: a furnace for heating a sample at an experimental heating rate; a monitoring device for monitoring the sample and producing a first signal indicating a relationship between a variation in a physical property of the sample and temperature; and a processor for processing the first signal by obtaining peak components of the first signal, calculating activation energy values based on the peak components of the first signal, and estimating a second signal that would be obtained by heating the sample at a heating rate different from the experimental heating rate.

42. A thermal analyzer according to claim 41; wherein the processor estimates the second signal based on the experimental heating rate, the first signal and the activation energy values.

43. A thermal analyzer according to claim 41; wherein the experimental heating rate is faster than the desired heating rate, so that the second signal may be estimated by performing an accelerated heating of the sample.

44. A thermal analyzer according to claim 41; wherein the furnace has an internal chamber having a sample support movable in response to decomposition of the sample, a symmetrically arranged reference substance support movable in response to decomposition of a reference substance, and means for maintaining the sample support and the reference substance support in a constant orientation and outputting the first signal corresponding to a relative amount of control required to maintain the sample support in the constant orientation.

45. A thermal analyzer according to claim 44; wherein the furnace further comprises a function generator for outputting a temperature control signal to control the furnace temperature according to a predetermined temperature control program, and for outputting an elapsed time signal.

46. A thermal analyzer according to claim 45; wherein the temperature control program comprises a start temperature at which thermal analysis of the sample is to begin, an end temperature at which the thermal analysis is to end, and a temperature rate at which the temperature of the sample is to be increased during the thermal analysis.

47. A thermal analyzer according to claim 41; wherein the processor includes means for separating the first signal into a plurality of components by calculating a second order derivative of the first signal, assigning as peak regions those regions of the first signal where the value of the second order derivative deviates outside a threshold range, and subtracting a baseline component of the first signal from the first signal to obtain the peak components.

48. A thermal analyzer according to claim 41; wherein the processor includes means for separating the peak components into a plurality of peak elements and outputting peak data.

49. A thermal analyzer according to claim 48; wherein the means for separating comprises differentiating means for taking the second-order derivative and the third-order derivative of the peak components with respect to time, assigning as a peak position of the first signal each point at which the third-order derivative of the peak components is equal to zero and, at the same time, the second-order derivative signal has a negative minimum value, counting the number of peak positions and separating overlapping peaks using an overlapping waveform-analyzing procedure.

50. A thermal analyzer according to claim 49; further comprising means for integrating peak data with respect to time.

51. A thermal analyzer according to claim 50; wherein the processor includes means for calculating the activation energy values of the separated peak components based on the temperature, peak data and peak integration data.

52. A thermal analyzer according to claim 41; wherein the processor includes a heating rate conversion and output device comprising means for calculating a peak shift, amplifying a baseline and adding data.

* * * * *